(12) United States Patent
Sánchez Ramírez et al.

(10) Patent No.: US 12,019,073 B2
(45) Date of Patent: Jun. 25, 2024

(54) METHOD FOR THE TREATMENT OF PATIENTS WITH CARCINOMAS

(71) Applicant: CENTRO DE INMUNOLOGIA MOLECULAR, Havana (CU)

(72) Inventors: Belinda Sánchez Ramírez, Havana (CU); Gretchen Báez Bergado, Havana (CU); Narjara González Suárez, Havana (CU); Mabel Cruz Rodríguez, Havana (CU); Diana Rosa Hernández Fernández, Havana (CU); Lisset Chao García, Sancti Spiritus (CU)

(73) Assignee: CENTRO DE INMUNOLOGIA MOLECULAR, Havana (CU)

( * ) Notice: Subject to any disclaimer, the term of this patent is extended or adjusted under 35 U.S.C. 154(b) by 0 days.

(21) Appl. No.: 16/494,102

(22) PCT Filed: Mar. 8, 2018

(86) PCT No.: PCT/CY2018/050001
§ 371 (c)(1),
(2) Date: Sep. 13, 2019

(87) PCT Pub. No.: WO2018/166542
PCT Pub. Date: Sep. 20, 2018

(65) Prior Publication Data
US 2020/0011870 A1    Jan. 9, 2020

(30) Foreign Application Priority Data
Mar. 15, 2017   (CU) .................................. 2017-0028

(51) Int. Cl.
G01N 33/574   (2006.01)
A61K 39/00    (2006.01)
A61P 35/00    (2006.01)

(52) U.S. Cl.
CPC .................. G01N 33/57407 (2013.01); A61K 39/001106 (2018.08); A61P 35/00 (2018.01); A61K 2039/545 (2013.01); A61K 2039/55555 (2013.01); A61K 2039/70 (2013.01)

(58) Field of Classification Search
CPC ...... G01N 33/57407; A61K 39/001106; A61K 2039/545; A61K 2039/70
See application file for complete search history.

(56) References Cited

U.S. PATENT DOCUMENTS 7,776,342 B2 *   8/2010   Fernandez Molina .   A61P 37/06
                                                424/249.1
2004/0229294 A1 *  11/2004 Chan-Hui ..........   G01N 33/6842
                                                435/7.2

FOREIGN PATENT DOCUMENTS

EP    3028714 A1   6/2016
WO   2010131080 A1  11/2010
WO   2015014327 A1   2/2015

OTHER PUBLICATIONS

Yonemori et al., Immunohistochemical Expression of HER1, HER3, and HER4 in HER2-Positive Breast Cancer Patients Treated With Trastuzumab-Containing Neoadjuvant Chemotherapy, J. Surg. Oncol. 2010:101:222-227, Publication Date: Jan. 19, 2010 (Year: 2010).*
Scott et al., Antibody therapy of cancer, Nature Review Cancer, 12, 278-287, Publication Date: Apr. 2012 (Year: 2012).*
Allegra et al., American Society of Clinical Oncology Provisional Clinical Opinion, J of Clin Oncol 27:2091-2096, Publication Date: Feb. 2, 2009 (Year: 2009).*
Kawaguchi et al., Targeting EGFR and HER-2 with cetuximab- and trastuzumabmediated immunotherapy in oesophageal squamous cell carcinoma, British Journal of Cancer, 97, 494-501, Publication Date: Jul. 10, 2007 (Year: 2007).*
Miller et al., RAS mutations and oncogenesis: not all RAS mutations are created equally, Frontiers in Genetics, vol. 2, article 100, Publication Date: Jan. 2012 (Year: 2012).*
Gura, T., Systems for Identifying New Drugs Are Often Faulty, Science, 1997, 278:1041-1042 (Year: 1997).*
Kaiser, J., First pass at cancer genoome reveals complex landscape, Science, 2006, 313:1370 (Year: 2006).*
Chames et al., Therapeutic antibodies: successes, limitations and hopes for the future, British J. of Pharmacology, 2009, 157, 220-233 (Year: 2009).*
Helfrich et al., AntitumorActivity of the Epidermal Growth Factor Receptor (EGFR) Tyrosine Kinase Inhibitor Gefitinib (ZD1839, Iressa) in Non-Small Cell Lung Cancer Cell Lines, Clin. Cancer Res., 12(23): 7117-7125, Publication Date: Dec. 1, 2006 (Year: 2006).*
Akashi et al., Enhancement of the antitumor activity of ionising radiation by nimotuzumab, a humanised monoclonal antibody to the epidermal growth factor receptor, in non-small cell lung cancer cell lines of differing epidermal growth, British Journal of Cancer, 98: 749-755, Published Date: Feb. 5, 2008 (Year: 2008).*
Ullrich, Axel, et al. "Human Epidermal Growth Factor Receptor cDNA Sequence and Aberrant Expression of the Amplified Gene in A431 Epidermoid Carcinoma Cells." Nature, vol. 309.5967 pp. 418-425 (1984).

(Continued)

*Primary Examiner* — Peter J Reddig
*Assistant Examiner* — Cheng Lu
(74) *Attorney, Agent, or Firm* — Hoffmann & Baron, LLP

(57) ABSTRACT

The present invention relates to the branch of Biotechnology and Medicine, particularly to a method for the selection and treatment of patients with carcinomas of epithelial origin that co-express the HER1 and HER2 receptors without increased expression of these receptors or with the presence of RAS activating mutations. In particular, this method is based on the application of bivalent vaccine compositions which have as active principle the extracellular domains of the HER1 and HER2 receptors or portions thereof and as an adjuvant the very small proteoliposomes derived from the outer membrane proteins of *Neisseria meningitidis* and the GM3 ganglioside. This method is useful for the treatment of patients whose expression levels of HER1 and HER2 do not allow the monoclonal antibodies against HER1 and/or HER2 to have a therapeutic effect.

3 Claims, 9 Drawing Sheets

(56) References Cited

OTHER PUBLICATIONS

Coussens, Lisa, et al. "Tyrosine Kinase Receptor with Extensive Homology to EGF Receptor Shares Chromosomal Location with Neu Oncogene," Science, vol. 230, pp. 1132-1139 (1985).
Seshacharyulu, Parthasarathy, et al. "Targeting the EGFR Signaling Pathway in Cancer Therapy," Expert Opinion on Therapeutic Targets, vol. 16, No. 1, pp. 15-31 (2012).
Pinkas-Kramarski, Ronit, et al. "Diversification of Neu Differentiation Factor and Epidermal Growth Factor Signaling by Combinatorial Receptor Interaction,." The EMBO Journal, vol. 15, No. 10, pp. 2452-2467 (1996).
Citri, Ami, et al., "EGF-ERBB Signalling: Towards the Systems Level," Nature Reviews Molecular Cell Biology, vol. 7.7, pp. 505-516 (Jul. 2006).
Faber, Anthony C., et al. "Differential Induction of Apoptosis in HER2 and EGFR Addicted Cancers Following PI3K Inhibition," Proceedings of the National Academy of Sciences, vol. 106, No. 46, pp. 19503-19508 (Nov. 17, 2009).
Murray, Peter J., "The JAK-STAT Signaling Pathway: Input and Output Integration," The Journal of Immunology, vol. 178, No. 5, pp. 2623-2629 (2007).
Yarden, Yosef, et al., "Untangling the ErbB Signalling Network," Nature Reviews Molecular Cell Biology, vol. 2, No. 2, pp. 127-137 (Feb. 2001).
Ross, Jeffrey S., et al. "The HER-2 Receptor and Breast Cancer: Ten Years of Targeted Anti-HER-2 Therapy and Personalized Medicine," The Oncologist, vol. 14, No. 4, pp. 320-368 (2009) (Parts 1 & 2).
Brand, Toni M., et al., "Molecular Mechanisms of Resistance to the EGFR Monoclonal Antibody Cetuximab," Cancer Biology & Therapy, vol. 11, No. 9, pp. 777-792 (May 2011).
Seth, D., et al. "Complex Post-Transcriptional Regulation of EGF-Receptor Expression by EGF and TGF-α in Human Prostate Cancer Cells," British Journal of Cancer, vol. 80, No. 5, pp. 657-669 (1999).
Neal, David E., et al., "Epidermal Growth Factor Receptor and Bladder Cancer: A Review," Urologia Internationalis, vol. 48, No. 4, pp. 365-371 (1992).
Gullick, William J., et al. "Expression of Epidermal Growth Factor Receptors on Human Cervical, Ovarian, and Vulval Carcinomas," Cancer Research, vol. 46, No. 1, pp. 285-292 (Jan. 1986).
Fichter, Christiane Daniela, et al. "EGFR, HER2 and HER3 Dimerization Patterns Guide Targeted Inhibition in Two Histotypes of Esophageal Cancer," International Journal of Cancer, vol. 135, No. 7, pp. 1517-1530 (2014).
Salomon, David S., et al. "Epidermal Growth Factor-Related Peptides and Their Receptors in Human Malignancies," Critical Reviews in Oncology/Hematology, vol. 19, No. 3, pp. 183-232 (1995).
Chow, Nan Haw, et al. "Significance of Urinary Epidermal Growth Factor and Its Receptor Expression in Human Bladder Cancer," Anticancer Research, vol. 17, No. 2B, pp. 1293-1296 (1997).
Grandis, Jennifer Rubin, et al. "Downmodulation of TGF-α Protein Expression with Antisense Oligonucleotides Inhibits Proliferation of Head and Neck Squamous Carcinoma but not Normal Mucosal Epithelial Cells," Journal of Cellular Biochemistry, vol. 69, No. 1, pp. 55-62 (1998).
Pal, Sumanta Kumar, et al. "Epidermal Growth Factor Receptor and Signal Transduction: Potential Targets for Anti-Cancer Therapy," Anti-Cancer Drugs, vol. 16, No. 5, pp. 483-494 (2005).
Tai, Wanyi, et al., "The Role of HER2 in Cancer Therapy and Targeted Drug Delivery," Journal of Controlled Release, vol. 146, No. 3, pp. 264-275 (Sep. 2010).
Suo, Zhenhe, et al. "EGFR Family Expression in Breast Carcinomas. c-erbB-2 and c-erbB-4 Receptors have Different effects on Survival," The Journal of Pathology: A Journal of the Pathological Society of Great Britain and Ireland, vol. 196, Issue 1, pp. 17-25 (Jan. 2002).
Di Lorenzo, Giuseppe, et al. "Expression of Epidermal Growth Factor Receptor Correlates with Disease Relapse and Progression to Androgen-Independence in Human Prostate Cancer," Clinical Cancer Research, vol. 8, No. 11, pp. 3438-3444 (Nov. 2002).
Emanuel, Stuart L., et al. "Cellular and in Vivo Activity of JNJ-28871063, a Nonquinazoline Pan-ErbB Kinase Inhibitor that Crosses the Blood-Brain Barrier and Displays Efficacy Against Intracranial Tumors," Molecular Pharmacology, vol. 73, No. 2, pp. 338-348 (2008).
Zhou, Yunfei, et al., "Synergy of Epidermal Growth Factor Receptor Kinase Inhibitor AG1478 and ErbB2 Kinase Inhibitor AG879 in Human Colon Carcinoma Cells is Associated with Induction of Apoptosis," Cancer Research, vol. 65, No. 13, pp. 5848-5856 (Jul. 2005).
Chen, Nan, et al. "Upregulation of PD-L1 by EGFR Activation Mediates the Immune Escape in EGFR-Driven NSCLC: Implication for Optional Immune Targeted Therapy for NSCLC Patients with EGFR Mutation," Journal of Thoracic Oncology, vol. 10, No. 6, pp. 910-923 (Jun. 2015).
Hartman, Zachary C., et al. "HER2 Overexpression Elicits a Proinflammatory IL-6 Autocrine Signaling Loop that is Critical for Tumorigenesis," Cancer Research, vol. 71, No. 13, pp. 4380-4391 (Jul. 2011).
Tortora, G., et al. "The Rationale for the Combination of Selective EGFR Inhibitors with Cytotoxic Drugs and Radiotherapy," The International Journal of Biological Markers, vol. 22, No. 1, Suppl. 4, pp. 47-52 (2007).
Schneider, Marlon R., et al., "The EGFR-HER2 Module: A Stem Cell Approach to Understanding a Prime Target and Driver of Solid Tumors," Oncogene, vol. 35, No. 23, pp. 2949-2960 (Sep. 2016).
Harding, Joanne, et al., "An Epidermal Growth Factor Receptor Chimeric Human-Murine Monoclonal Antibody," Drugs Today (Barc), vol. 41, pp. 107-127 (2005).
Mateo, Cristina, et al. "Humanization of a Mouse Monoclonal Antibody that Blocks the Epidermal Growth Factor Receptor: Recovery of Antagonistic Activity," Immunotechnology, vol. 3, No. 1, pp. 71-81 (1997).
Ramos-Suzarte, Mayra, et al., "Treatment of Malignant, Non-Resectable, Epithelial Origin Esophageal Tumours with the Humanized Anti-Epidermal Growth Factor Antibody Nimotuzumab Combined with Radiation Therapy and Chemotherapy," Cancer Biology & Therapy, vol. 13, No. 8, pp. 600-605 (Jun. 2012).
Garrido, Greta, et al. "Bivalent Binding by Intermediate Affinity of Nimotuzumab: A Contribution to Explain Antibody Clinical Profile," Cancer Biology & Therapy, vol. 11, No. 4, pp. 373-382 (Feb. 2011).
Slamon, Dennis J., et al. "Use of Chemotherapy Plus A Monoclonal Antibody Against HER2 for Metastatic Breast Cancer that Overexpresses HER2," New England Journal of Medicine, vol. 344, No. 11, pp. 783-792 (Mar. 2001).
Yarden, Yosef, et al., "The ERBB Network: At Last, Cancer Therapy Meets Systems Biology," Nature Reviews Cancer, vol. 12, No. 8, pp. 553-563 (2012).
Grøvdal, Lene Meisaether, et al. "EGF Receptor Inhibitors Increase ErbB3 mRNA and Protein Levels in Breast Cancer Cells," Cellular Signalling, vol. 24, No. 1, pp. 296-301 (2012).
Maron, Ruth et al. "Inhibition of Pancreatic Carcinoma by Homo- and Heterocombinations of Antibodies Against EGF-Receptor and Its Kin HER2/ErbB-2," Proceedings of the National Academy of Sciences, vol. 110, No. 38, pp. 15389-15394 (Sep. 2013).
Yarden, Yosef, et al., "Cancer Immunotherapy: More is (Much) Better," Clinical Cancer Research, vol. 21, No. 18, pp. 4030-4032 (Sep. 2015).
Assenat, Eric, et al. "Dual Targeting of HER1/EGFR and HER2 with Cetuximab and Trastuzumab in Patients with Metastatic Pancreatic Cancer After Gemcitabine Failure: Results of the "Therapy" Phase 1-2 Tria,." Oncotarget, vol. 6, No. 14, pp. 12796-12808 (2015).
Eisenhauer, Elizabeth A., et al. "New Response Evaluation Criteria in Solid Tumours: Revised RECIST Guideline (Version 1.1)," European Journal of Cancer, vol. 45, No. 2, pp. 228-247 (2009).
Ben-Kasus, Tsipi, et al. "Persistent Elimination of ErbB-2/HER2-Overexpressing Tumors Using Combinations of Monoclonal Antibodies: Relevance of Receptor Endocytosis," Proceedings of the National Academy of Sciences, vol. 106, No. 9, pp. 3294-3299 (2009).

(56) References Cited

OTHER PUBLICATIONS

Suárez, Narjara González, et al. "Anti-Proliferative and Pro-Apoptotic Effects Induced by Simultaneous Inactivation of HER1 and HER2 Through Endogenous Polyclonal Antibodies," Oncotarget, vol. 8, No. 47, pp. 82872-82884 (2017).

Schneider, Maron R., et al., "The EGFR-HER2 Module: A Stem Cell Approach to Understanding a Prime Target and Driver of Solid Tumors," Oncogene, vol. 35, No. 23, pp. 2949-2960 (2016).

Bahrami, A., et al., "Targeting RAS signaling Pathway as a Potential Therapeutic Target in the Treatment of Colorectal Cancer," Journal of Cellular Physiology, vol. 233, pp. 2058-2066, (Mar. 2017), DOI: 10.1002/jcp.25890.

Stevens, Michiel, et al. "Optimal Halbach Configuration for Flow-through Immunomagnetic CTC Enrichment." Diagnostics, vol. 11, No. 6, p. 1020 (2021), https://doi.org/10.3390/diagnostics11061020.

\* cited by examiner

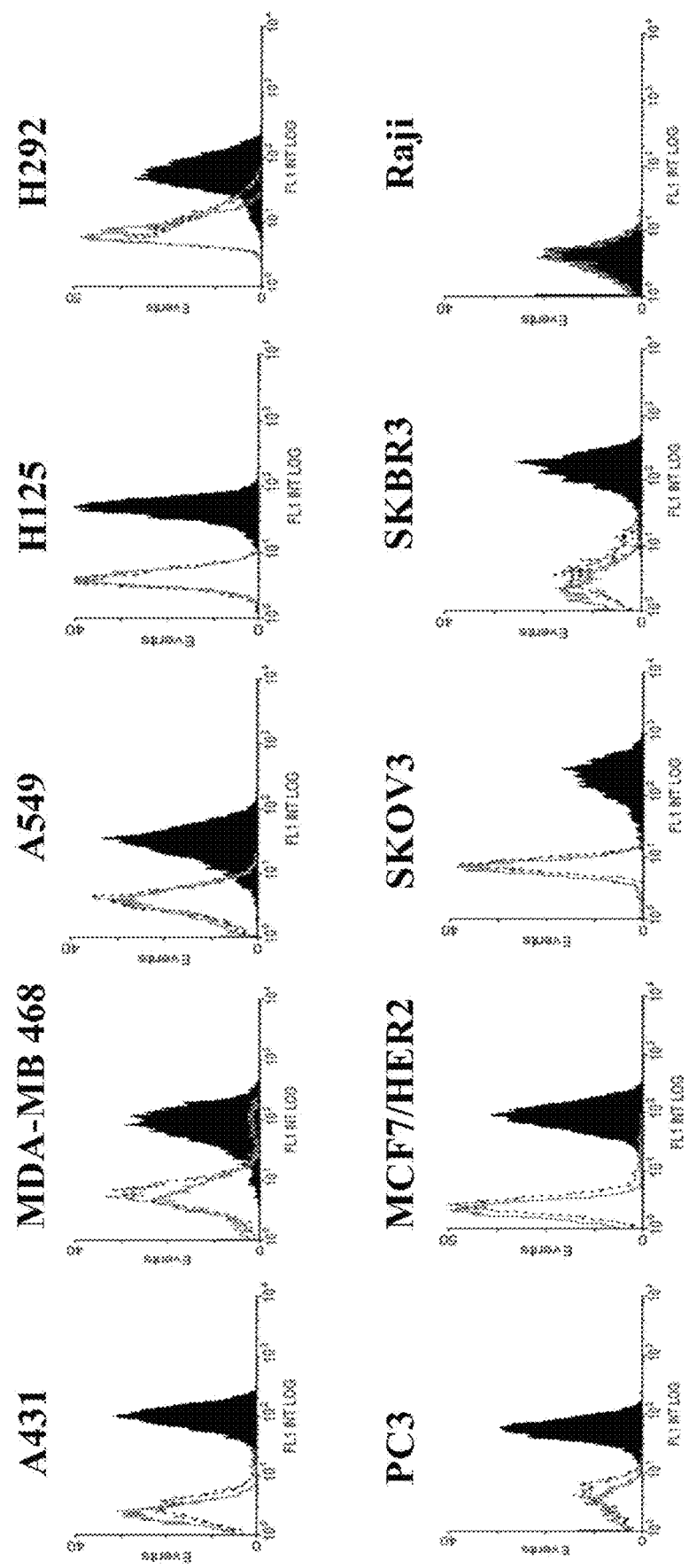

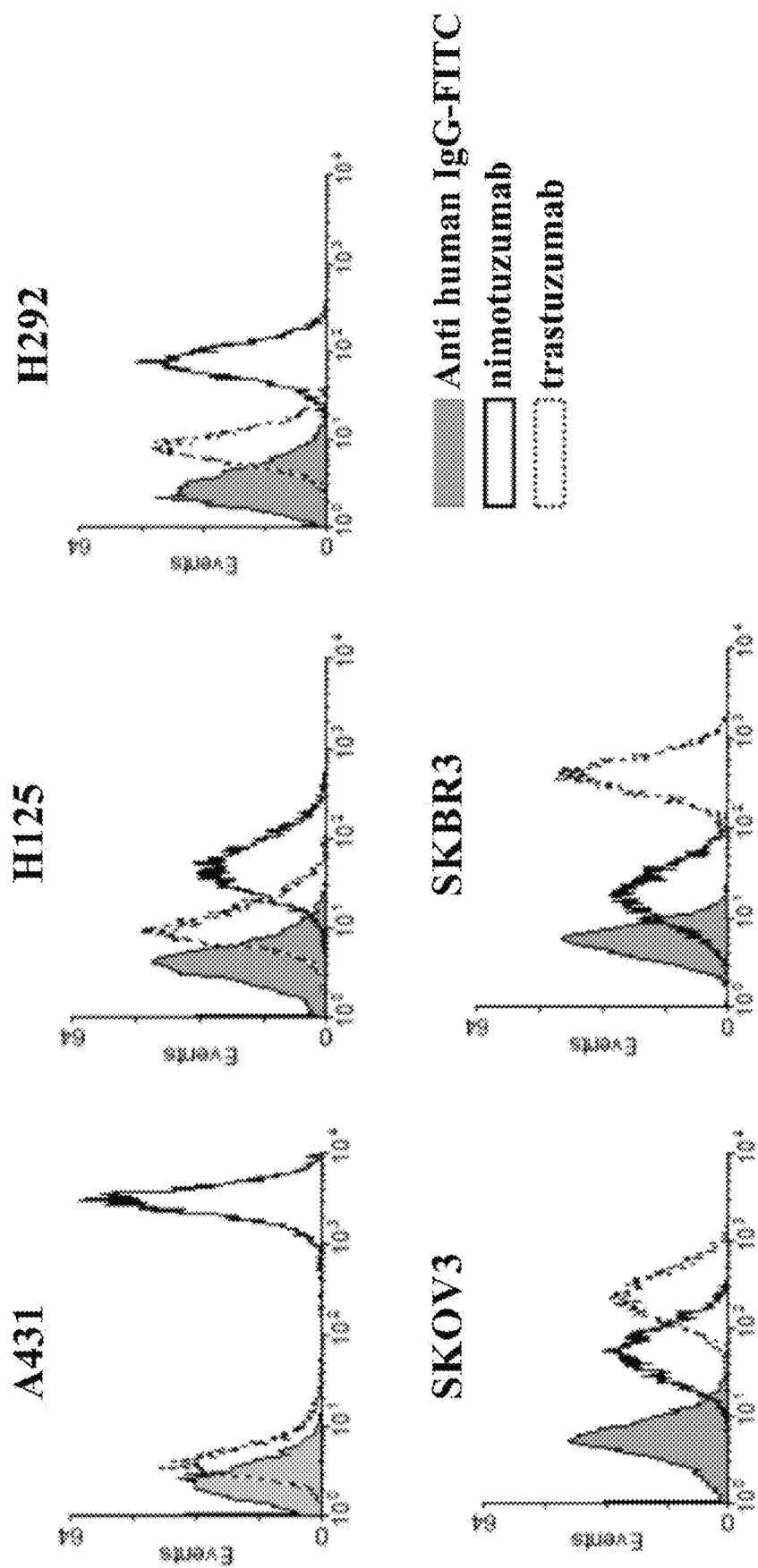

NT: non treatment
n: nimotuzumab 10 µg/mL
t: trastuzumab 1 µg/mL
n+t: 10 µg/mL total
PI: preimmune sera
BV: bivalent vaccine
MitC: mitomicine C

METHOD FOR THE TREATMENT OF PATIENTS WITH CARCINOMAS

CROSS-REFERENCE TO RELATED APPLICATIONS

This application is a National Stage Application that claims a benefit of priority from Application No. PCT/CU2018/05000 filed Mar. 8, 2018, which claims priority to Application No. CU 2017-0028, filed Mar. 25, 2017.

SCOPE OF THE TECHNIQUE

The present invention relates to the field of Biotechnology and Medicine. In particular, it relates to methods for improving the treatment of a certain subgroup of patients with carcinomas of epithelial origin, mainly to those patients who are not candidates for receiving monoclonal antibody therapy against HER-1 or HER-2. In a particular embodiment the invention provides a method of treatment wherein the patients selected are treated with bivalent vaccine compositions of HER1+HER2.

BACKGROUND

The receptors of the epidermal growth factor receptor (EGFR) family, with tyrosine kinase activity, are involved in growth, differentiation, motility and survival of cells (Schneider M R and Yarden Y. (2016) Oncogene 35 (23): 2949-60). This family consists of four members: the prototype is the EGFR (HER1/ErbB1), which was the first receptor with tyrosine kinase activity cloned (Ullrich A., Coussens L., Hayflick J S et al (1984) Nature 309 (5967): 418-25), HER2/Neu/ErbB2 (Coussens L., Yang-Feng T L, Liao Y C et al (1985) Science 230 (4730): 1132-39), HER3/ErbB3 and HER4/ErbB4. The characteristic structure of these receptors consists of an N-terminal extracellular ligand-binding domain that contains the dimerization arm, a hydrophobic transmembrane region and a C-terminal cytoplasmic region exhibiting tyrosine kinase activity, in addition to several residues of autophosphorylation. Frequently, these receptors are co-expressed in various combinations, and depending on the activating ligand they can form homodimers or heterodimers, generating a complex network of signal transduction (Seshacharyulu P., Ponnusamy M P, Haridas D., et al (2012) Expert Opin Ther Targets 16 (1): 15-31. In this sense, it has been reported that heterodimeric combinations constitute the most potent signaling complexes and are characterized by their direct control over the cell cycle (Pinkas-Kramarski R., Soussan L., Waterman H. et al (1996) EMBO J 15 (10): 2452-67.

The phosphotyrosine residues generated in the activation of HER/ErbB receptors, recruit adapter proteins that initiate multiple intracellular signaling pathways, closely related to each other, which determines the great complexity of the signal network transmitted through HER1 and HER2. The first of these signaling cascades is the pathway of mitogen-activated protein kinases (MAPKs) whose aberrant activity is related to the uncontrolled cell proliferation observed in tumors (Citri A. and Yarden Y. (2006) Nat Rev Mol Cell Biol 7 (7): 505-16). Another of the signaling cascades is the phosphatidylinositol 3 kinase pathway (PI3K/Akt, "phosphotidylinositol-3 kinase/serine-threonine protein kinase"), whose activation leads to an increase in anti-apoptotic signals mediated by NF-κB and cell division, and therefore is directly related to the evasion of apoptosis by tumor cells (Faber A C, Li D., Song Y, et al (2009) Proc Natl Acad Sci USA 106 (46): 19503-08. The third signaling pathway is related to the c-Src adapter protein, which activates the family of the transcription factor and signal transducer 3 (STAT3, signal transducer and activator of transcription 3), which activates processes such as proliferation, angiogenesis and inflammation associated with tumors (Murray P J (2007) J Immunol 178 (5): 2623-29).

The HER1 and HER2 receptors are involved in the progression of tumors of epithelial origin. These proteins are expressed in the epithelial tissues of the body. However, due to their aberrant expression in many types of tumors of epithelial origin as well as their functional relevance in the uncontrolled proliferation of malignant cells, they have been considered tumor-associated antigens (Yarden Y. and Sliwkowski M X (2001) Nat Rev Mol Cell Bio 2, 127-137 (127-37) and (Ross J S, Slodkowska E A, Symmans W F et al (2009) Oncologist 14 (4): 320-68).

HER1 has an increased expression in tumors of lung, breast, head and neck, colon, pancreas (Brand T M, Iida M. and Wheeler D L (2011) Cancer Biol Ther 11 (9): 777-92.), prostate (Seth D., Shaw K., Jazayeri J. et al (1999) Br J Cancer 80 (5-6): 657-69.), bladder (Neal D E and Mellon K. (1992) Urol Int 48 (4): 365-71), ovary (Gullick W J, Marsden J J, Whittle N. et al (1986) Cancer Res 46 (1): 285-92), esophagus (Fitcher, C D Timme S., Braun J A et al., (2014) Int. J. Cancer, 135, 1517-30) and glioma (Salomon D S, Brandt R., Ciardiello F. et al (1995) Crit Rev Oncol Hematol 19 (3): 183-32.). It should be noted that the frequency of HER1 overexpression in the mentioned carcinomas is high and has been associated with a poor prognosis of the disease in tumors of the head and neck and lung, with a high risk of recurrence of the disease (Chow N H, Liu H S, Lee E I et al (1997) Anticancer Res 17 (2B): 1293-96) and with decreased survival in patients with ovarian, colon, bladder, thyroid and head and neck cancer (Grandis J R, Chakraborty A., Zeng Q., et al (1998) J Cell Biochem 69 (1): 55-62.). In addition, high levels of HER1 correlate with resistance to conventional therapies such as chemo and radiotherapy (Pal S. K. and Pegram M. (2005) Anticancer Drugs 16 (5): 483-94).

In addition, HER2 is found in high levels in tumors of the breast, gastric, lung, ovarian, and prostate tumors (Tai W., Mahato R. and Cheng K. (2010) J Control Release 146 (3): 264-75) and its overexpression in breast tumors has been correlated with a decrease in the overall survival of patients.

Overexpression of HER2 in breast tumors has been correlated with a decrease in overall survival. Besides, the co-expression of HER1 and HER2 in these tumors markedly increases this risk, which suggests that the expression of HER1 in these carcinomas has a synergistic effect on the clinical influence of HER2 expression (Suo Z., Risberg B., Kalsson M G et al (2002) J Pathol 196 (1): 17-25).

The co-expression of HER1 and HER2 has been verified in other locations, for example: cancer of the brain, ovary, head and neck, lung and prostate (Di Lorenzo G., Tortora G., D'Armiento F P, et al. 2002) Clin Cancer Res 8 (11): 3438-44 and Emanuel S L, Hughes T V, Adams M., et al (2008) Mol Pharmacol 73 (2): 338-48). This co-expression has been associated to poor prognosis of the disease and to a tumor phenotype characterized by strong signals of survival transmitted by the HER1-HER2 heterodimer (Zhou Y. and Brattain M G (2005) Cancer Res 65 (13): 5848-56). The co-expression of HER1 and HER2 is not necessarily accompanied by increased expression of one of these receptors. In fact, the overexpression of a receptor of the family tilts the balance towards the formation of homodimers of said receptor, and against the formation of heterodimers with the receptor that is co-expressed. On the contrary, a low or intermediate expression of these receptors co-expressed in tumor cells leads to a greater formation of heterodimers. The cells with these characteristics are more dependent on heterodimers to activate the cell signaling pathways MAPK, STAT3 and PI3K/AKT (Fichter C D, Timme S., Braun J A, (2014) Int J Cancer. October 1; 135 (7): 1517-30).

Coupled with the solid clinical evidence supporting the relevance of the expression of HER1 and HER2 in the proliferation and survival of epithelial tumors, numerous studies validate the fundamental role of both receptors in the regulation of other attributes of tumors such as inflammation and escape. Tumor, among others (Chen N., Fang W., Zhan J., et al., (2015) J Thorac Oncol, 2015 June; 10 (6): 910-23 and Hartman Z C, Yang X Y, Glass O., (2011) Cancer Res. July 1; 71 (13): 4380-91.

Several therapies have been developed to inhibit the pro-tumoral activity of HER1 and HER2 receptors. The drugs inhibitors of the tyrosine kinase activity (TKI) of HER1 and/or HER2 are drugs of low molecular weight analogous to triphosphate of adenosine (ATP) which has already been widely tested in the clinic. Although these drugs have shown promising results, their high toxicity has limited chronic use. The TKI gefitinib (Iressa), erlotinib (Tarceva) and afatinib (Gilotrif) selectively inhibit HER1 by blocking the ATP binding site, located in the intracellular domain (Tortora G., Gelardi T., Ciardiello F. (2007) Int J Biot Markers January-March; 22 (1 Suppl 4): S47-52). The mentioned inhibitors have been approved for the treatment of patients with non-small cell lung carcinomas expressing the HER1 receptor in its mutated form (L858R mutation in exon 21 of the ErbB oncogene) and with an increased sensitivity to this type of drug (Schneider M R and Yarden Y. (2016) Oncogene 35 (23): 2949-60).

Additionally, three monoclonal antibodies (MAbs) directed against HER1-ECD have been registered for use in the clinic. The chimeric MAb of isotype IgG1, cetuximab (Erbitux) is the most successful anti-HER1 therapy so far. It binds to subdomain III of HER1-ECD with high affinity for the receptor (Kd=2.3×10-9M) thus preventing ligand binding and receptor activation (Harding J. and Burtness B. (2005) Drugs Today (Barc) 41 (2): 107-27). This anti-HER1 MAb has been approved for the treatment of metastatic colon cancer with detectable expression of HER1, and without RAS activating mutations, as well as for the treatment of squamous carcinomas of the head and neck, after chemotherapy or combined with radio or chemotherapy (Seshacharyulu P., Ponnusamy M P, Haridas D., et al (2012) Expert Opin Ther Targets 16 (1): 15-31). Another anti-HER1 MAb registered for the treatment of metastatic colorectal carcinoma without activating expression of RAS and administered in combination with chemotherapy is panitumumab (Vectibix), which is a human IgG2 that recognizes HER1-ECD with more affinity than cetuximab (Seshacharyulu P., Ponnusamy M P, Haridas D., et al (2012) Expert Opin Ther Targets 16 (1): 15-31). Finally, the humanized mAb nimotuzumab (TheraCIM®), IgG1, recognizes the subdomain III of HER1-ECD (Mateo C., Moreno E., Amour K. et al (1997) Immunotechnology 3 (1): 71-81), with an intermediate affinity, (Kd nimotuzumab=2.1×10-8M) blocking the binding of the ligand and consequently the signaling through HER1. This MAb is registered for use in patients with advanced head and neck tumors, glioma, esophagus and nasopharyngeal tumors (Ramos-Suzarte M., Lorenzo-Luaces P., Lazo N G, et al (2012) Cancer Biol Ther 13 (8): 600-05). Due to its low toxicity, this antibody is used in chronic treatments (Garrido G., Tikhomirov I. A., Rabasa A., et al (2011a) Cancer Biol Ther 11 (4): 373-82). Although the results obtained with all these anti-HER1 therapies have benefited a niche of patients, there is another group of patients that are not suitable candidates for them. Somatic mutations of RAS that provide transformed cells with proliferative advantages are among the most frequent events of tumorigenesis (KRAS, HRAS and NRAS). The frequency of these mutations is very high in tumors of pancreas, colon, lung, gastric, and others (Bahrami A, Hassanian S M, ShahidSales S., et al (2017) J Cell Physiol. March 6. doi: 10.1002/jcp.25890).

HER2 specific MAbs are also registered for the treatment of cancer patients. The trastuzumab (Herceptin)MAb, specific for the IV subdomain of the ECD of HER2, is indicated for adjuvant treatment of patients with breast, gastric and pancreatic tumors that overexpress the HER2 molecule. Additionally, this mAb has been covalently conjugated to a chemotherapeutic drug to enhance its antitumor effect, which has resulted in a new therapy, called trastuzumab-DM1 (Kadcyla), recently approved for the treatment of metastatic breast carcinoma patients refractory to treatment with trastuzumab and chemotherapy. (Slamon D J, Leyland-Jones B., Shak S., et al (2001) N Engl J Med 344 (11): 783-92). Another humanized mAb specific for subdomain II of HER2 ECD is pertuzumab (Perjeta), which is indicated for the treatment of patients with breast cancer, in combination with trastuzumab.

The complex biology of tumors results in mechanisms of resistance to monotherapies against HER1 and HER2 (Yarden Y. and Pines G. (2012) Nat Rev Cancer 12 (8): 553-63) and (Brand T M, Iida M. and Wheeler D L (2011) Cancer Biol Ther 11 (9): 777-92). Overexpression of other members of the HER/ErbB family has been described among the resistance mechanisms frequently observed in the clinic to these anti-HER1 or anti-HER2 treatments (Grovdal L M, Kim J., Holst M R, et al. 2012) Cell Signal 24 (1): 296-301). This has conducted to the evaluation of combinations targeting different epitopes of the same receptor or more than one receptor in the family, which have been shown to be more effective in the inhibition of the signaling cascades, endocytosis of the receptors and therefore have a greater antitumor effect. (Maron R., Schechter B., Mancini M., et al. (2013) Proc Natl Acad Sci USA. September 17; 110 (38): 15389-94 and (Yarden Y. and Sela M. (2015) Clin Cancer Res 21 (18): 4030-32. In the clinic stage the combination of MAbs trastuzumab and cetuximab was evaluated in order to demonstrate its superiority in patients with pancreatic carcinoma refractory to gencitabine. In spite of the promising results obtained, the implementation of these therapies has produced an increase in toxicity (Assenat E., Azria D., Mollevi C., et al (2015) Oncotarget 6 (14): 12796-808).

Although the mentioned registered therapies have contributed to increase the survival of a group of cancer patients, there is still a niche of patients that do not benefit from their use. Among this type of patients are those who present tumors with activating mutations of the RAS protein, as well as those whose tumors co-express the HER1 and HER2 receptors but do not have overexpression or increased expression of them. In U.S. Pat. No. 7,776,342 and WO 2015/014327, bivalent vaccine (BV) compositions which comprise as active principle the extracellular domains of the HER1 and HER2 receptors and as adjuvant the very small sized proteoliposomes derived from outer membrane proteins of *Neisseria meningitidis* containing the ganglioside GM3 are claimed. Unexpectedly, the inventors of the present invention found that the above-mentioned vaccine compositions have an effect on carcinomas of epithelial origin that co-express the HER1 and HER2 receptors without increased expression of them or in those with RAS activating mutations and that the effect is superior to the one observed when administering the MAbs against HER1 and HER2 registered for use in the clinic.

SUMMARY OF THE INVENTION

In one embodiment the present invention is based on a method for determining whether a patient diagnosed with carcinoma of epithelial origin is likely to respond to treatment with an EGFR family inhibitor that comprises a step for determining in a sample taken from this type of patient the presence of at least one of the biomarkers selected from the group that includes: co-expression of the HER1 and HER2 receptors and their expression levels or the existence of activating mutations in RAS.

In a particular embodiment it is concluded that the patient will be considered a responder to the treatment if he has co-expression of the HER1 and HER2 receptors without increased expression of them or has activating mutations in RAS.

More particularly, those patients whose samples have a level of expression of HER1 and HER2 of 1+ or 2+ measured by immunohistochemistry (IHC) will be considered as responders.

Another object of the present invention is a method for treating a patient with carcinoma of epithelial origin comprising the determination of whether a patient with the above-mentioned diagnosis is likely to respond to treatment with an inhibitor of the EGFR family and the administration to this patient of a therapeutically effective amount of said inhibitor.

Particularly, the inhibitor of the EGFR family is the BV that has as active principle the complete extracellular domains of the HER1 and HER2 receptors or portions thereof and as adjuvant the very small sized proteoliposomes derived from outer membrane proteins of *Neisseria meningitidis* containing the ganglioside GM3. The above-mentioned vaccine is used in a range of doses of the extracellular domains of HER1 and HER2 or portions thereof that is between 400 µg to 1600 µg; this concentration being the sum of both molecules. The vaccine is administered subcutaneously, intradermal or intramuscularly weekly during the first five doses followed by monthly doses of maintenance by at least six months. After these administrations, responder patients show a complete or partial response after 9 doses of the administration of the BV.

In particular, the treatment method object of the present invention is used for the treatment of squamous epithelial cells cancer, small cell lung cancer, non-small cell lung cancer, lung adenocarcinoma, squamous cell carcinoma of the lung, hepatocellular cancer, gastric, gastrointestinal, pancreas, gliobastoma, cervical, ovarian, liver, bladder, breast, colon, rectum, colorectal cancer, head and neck, uterus, salivary gland carcinoma, kidney, prostate, vulva, thyroid, anal carcinoma, carcinoma of the penis.

DETAILED DESCRIPTION OF THE INVENTION

Pharmaceutical Compositions.

The pharmaceutical compositions that are used in the present invention comprise as active principle the extracellular domains of the HER1 and HER2 receptors or portions thereof and as adjuvant it uses the small sized proteoliposomes derived from outer membrane proteins of *Neisseria meningitidis* and GM3 ganglioside (VSSP-GM3).

In a particular embodiment the vaccine compositions employed in the present invention may additionally comprise other pharmaceutically suitable adjuvant. These adjuvants may be but are not limited to, an oily adjuvant such as highly purified mineral oil and a mineral adjuvant such as Alumina.

In addition, the vaccine compositions used herein contain suitable excipients which include, for example: water, saline solution and the similars.

Methods of Identification and/or Selection of Tumors for the Application of the HER1+HER2 BV Compositions.

For the selection of tumors in which the HER1+HER2 BV compositions will have a therapeutic effect, the level of expression of the HER receptors or the presence of RAS mutations in the samples is determined. Sources for obtaining tumor samples include but are not limited to tumor biopsies, circulating tumor cells, circulating plasma proteins, ascites fluid and circulating DNA.

A tumor cell with increased expression of HER receptors is one that has higher levels of this molecule as compared to a non-tumor cell of the same cell type. Increased expression of HER receptors can be determined by a diagnostic or prognostic assay that evaluates whether there are increased levels of the receptor in the cell surface, for example IHC, immunofluorescence or polymerase chain reaction.

In contrast, a tumor cell that does not have increased expression of HER receptors is the one that has higher than normal levels of HER receptors proteins or genes as compared to a non-tumor cell of the same cell type but that does not have considerably increased levels of said expression.

To determine the levels of expression of HER1 and HER2 receptors in samples of tumor tissues, various diagnostic/prognostic systems are available. Some examples are IHC techniques such as HERCEPTEST-Dako and EGFR pharmDxTM-Dako. Paraffin embedded tissues can be classified by the intensity of the IHC labeling as follows:

Negative or Score 0. No staining by IHC is observed or the staining is in less than 10% of the tumor cells.

Negative/Weak or Score 1+. Tenuous staining is observed in more than 10% of the tumor cells, but only in part of their membranes.

Weak/Moderate or Score 2+: Weak to moderate staining is observed in more than 10% of tumor cells, homogeneously in the membrane.

Intense or 3+ Score: Moderate to strong staining is observed in more than 10% of the tumor cells, homogeneously in the membrane.

Tumors with a score of 0 for HER1 and/or HER2 can be classified as having no detectable expression of these receptors. Tumors with a score between 1+ and 2+ for HER1 and/or HER2 can be classified as having no increased expression of these receptors. Tumors with a 3+ score for HER1 and/or HER2 can be classified as having increased expression of these receptors.

To determine RAS mutations, routine techniques known from the state of the art can be used. An example of this is to obtain a sample of the tumor of the patient and extract the nucleic acids from the sample that are amplified and sequenced. Another method is to obtain a sample of serum or plasma from the patient in which the circulating tumor cells are found with the RAS oncogene and their mutation is detected using microarrays or polymerase chain reaction. If a positive result of mutation of RAS in the plasma or serum is found it suggests a RAS mutation in the tumor, while the absence of RAS mutation in said plasma or serum does not necessarily prove the absence of a similar mutation in the tumor tissue. Additionally or alternatively, the expression of mutated RAS can be checked by determining the mutated polypeptides in the tumor sample using antibodies that bind to specific epitopes on said RAS mutant polypeptides. (Steven M A, Diagn. 2011; 11 (6): 635-642).

Treatment Methods.

In a first aspect, the present invention relates to a method of stratification of a subject diagnosed with cancer, specifically with carcinoma of epithelial origin, in responders or non-responders to treatment with the HER1+HER2 BV compositions. Applying said method, the expression levels of the HER1 and HER2 receptors or the presence of RAS activating mutations are determined in the patient. The co-expression of the HER1 and HER2 receptors without increased expression of them indicates that the subject will be responsive to the treatment with the HER1+HER2 BV compositions. It can also be predicted that the patient will respond to treatment with the aforementioned vaccine compositions if the presence of RAS activating mutations is confirmed in the sample.

In a particular embodiment, the present invention relates to a method for treating subjects with carcinoma of epithelial origin, previously classified as responders by the method described above and which comprises the administration to said patients of inhibitors of the EGFR family. Specifically, these inhibitors consist of BV compositions composed of the extracellular domains of the HER1 and HER2 receptors or portions thereof. The term "subject" refers to a human patient.

The term "responder" in the context of the method provided in the present invention means that the patient or tumor exhibit a complete or partial response after administration of the VB compositions herein defined, according to the Response Evaluation Criteria in Solid Tumors (RECIST) guideline. The term "non-responder" in the context of the present invention refers to those patients that show a stable or progressive disease after the administration of said vaccine compositions. RECIST guideline is described in: New response evaluation criteria in solid tumours: revised RECIST guideline (version 1.1). Eur. J. Cancer. 45, No. 2, 2009, 228-47.

In the context of the present invention, the term "therapeutic effect" in general refers to the desirable or beneficial impact of the treatment such as, for example, an improvement or remission in the manifestations of the disease. The term "manifestation" of the disease is used to describe its perceptible expression and includes both the clinical manifestations that can be detected during a medical examination and/or that are perceptible by the patient (symptoms) and the pathological manifestations that are the meaning of the expression of the disease at the cellular and molecular level.

The method of treatment of the present invention comprises a step of administration to a patient of an effective amount of VB compositions based on the combination of the HER1 and HER2 receptors. The term "effective amount" refers to the amount of the vaccine composition effective for treating cancer in the patient. The effective amount of the vaccine composition can reduce the number of cancer cells, reduce the size of the tumor; inhibit (either by reducing to a certain extent or preferably stopping) the infiltration of cancer cells into peripheral organs, tumor metastases, tumor growth and/or alleviating symptoms associated with cancer.

Among the types of cancer that can be treated with the method object of the present invention are carcinomas of epithelial origin. More particularly, examples of these cancers include squamous epithelial cell cancer, lung cancer (including small cell, non-small cell lung, lung adenocarcinoma and squamous cell carcinoma of the lung), hepatocellular cancer, gastric cancer including gastrointestinal, pancreatic cancer, head and neck gliobastoma, cervical, ovarian, liver, bladder, breast, colon, rectum, colorectal, uterus, salivary gland, kidney, prostate, vulva, thyroid, anal and penis cancer. In the method of the present invention the HER1+HER2 BV compositions can be administered by any known route, such as: subcutaneous, intradermal, intramuscular. Preferably subcutaneous route.

The dose range of the extracellular domains of HER1+HER2 or portions thereof to be employed in the patients that are eligible as responders for treatment with the vaccine compositions of the present invention is between 400 µg to 1600 µg, preferably 800 µg to 1600 µg; this concentration being the sum of both molecules. Said compositions are administered to the subjects with a biweekly frequency during at least a total of five induction doses and subsequently in monthly maintenance doses for at least six months.

BRIEF DESCRIPTION OF THE FIGURES

FIG. 1. Recognition by flow cytometry of tumor lines with different expression levels of HER1 and HER2: A431, MDAMB468, H125, H292, PC3, SKBR3, MCF7/HER2, SKOV3, A549 and Raji, by polyclonal antibodies (PAbs) generated by the HER1+HER2 BV.

FIGS. 2A-2C. Effect caused by the PAbs induced by the HER1+HER2 BV on cell viability: FIG. 2A) Flow cytometry performed to evaluate the recognition of the lines tested by MAbs trastuzumab and nimotuzumab. FIG. 2B) Inhibition of cell viability in cell lines A431, H125, H292, SKOV3, SKBR3 with differential expression of HER1 and HER2 measured by the colorimetric method MTT. FIG. 2C) Comparative bar graph of the effect of sera on cell viability in the different lines tested.

FIG. 7A) Degradation of HER1 after 24 hours of treatment. FIG. 7B) Degradation of HER2 after 1 h of treatment.

EXAMPLES

Example 1. Recognition of Tumor Lines HER1+HER2+ by the PAbs of the Immune Serum Induced by the HER1+HER2 BV Sera from mice immunized with the BV HER1+HER2 were diluted 1:200 and incubated for 20 min with $10^5$ cells from tumor lines that co-express the HER1 and HER2 receptors. Lines that do not have increased expression of any of these receptors were used: H125, derived from lung carcinoma; H292, derived from lung carcinoma; PC3, derived from prostate carcinoma. In addition, lines with increased expression of HER1 were used: A431, derived from vulvar epithelial carcinoma; MDAMB468, derived from breast carcinoma and lines with increased expression of HER2: SKBR3, derived from breast carcinoma; MCF7/HER2 derived from breast carcinoma transfected with HER2; SKOV3, derived from ovarian carcinoma. The KRAS mutated lung carcinoma A549 cell line was also used. The Raji line, derived from Burkitt's lymphoma, was used as a negative control of receptor expression. The pre-immune sera were used as negative specificity controls while nimotuzumab MAb, specific for HER1, and trastuzumab MAb, specific for HER2, were used as positive controls. The recognition was evaluated by flow cytometry. FIG. 1 shows that the sera generated by the BV recognized all the cell lines evaluated, and the highest intensity of the recognition (corresponding to the highest mean fluorescence intensity (MFI)), was observed in the lines with increased expression of some of the receptors.

Example 2. The PAbs of the Immune Serum Induced by the HER1+HER2 BV Inhibit the Viability of Tumor Lines with Differential Expression of HER1 and HER2

The Effect is More Marked in Lines that do not Show Increased Expression of these Receptors.

To evaluate the effect of immune sera on lines with different expression levels of HER1 and HER2 as shown in Table 1, these levels were first corroborated using the mAbs trastuzumab and nimotuzumab, specific for HER2 and HER1 respectively. For this, the cells of the human tumor lines: A431, H125, H292, SKOV3 and SKBR3 were incubated for 20 min with the above-mentioned mAbs and the MFI was measured. The overlapping histograms of the recognition of the MAbs specific for HER1 and HER2 are shown in FIG. 2A. It has been reported in the literature that the flow cytometry of staining cell lines and the IHC of the patient's tumors are associated (Helfrich B A, et al., (2006) Clin Cancer Res; 12 (23) December 1; 7117-25), which allows us to extrapolate our results.

Figure 2B:
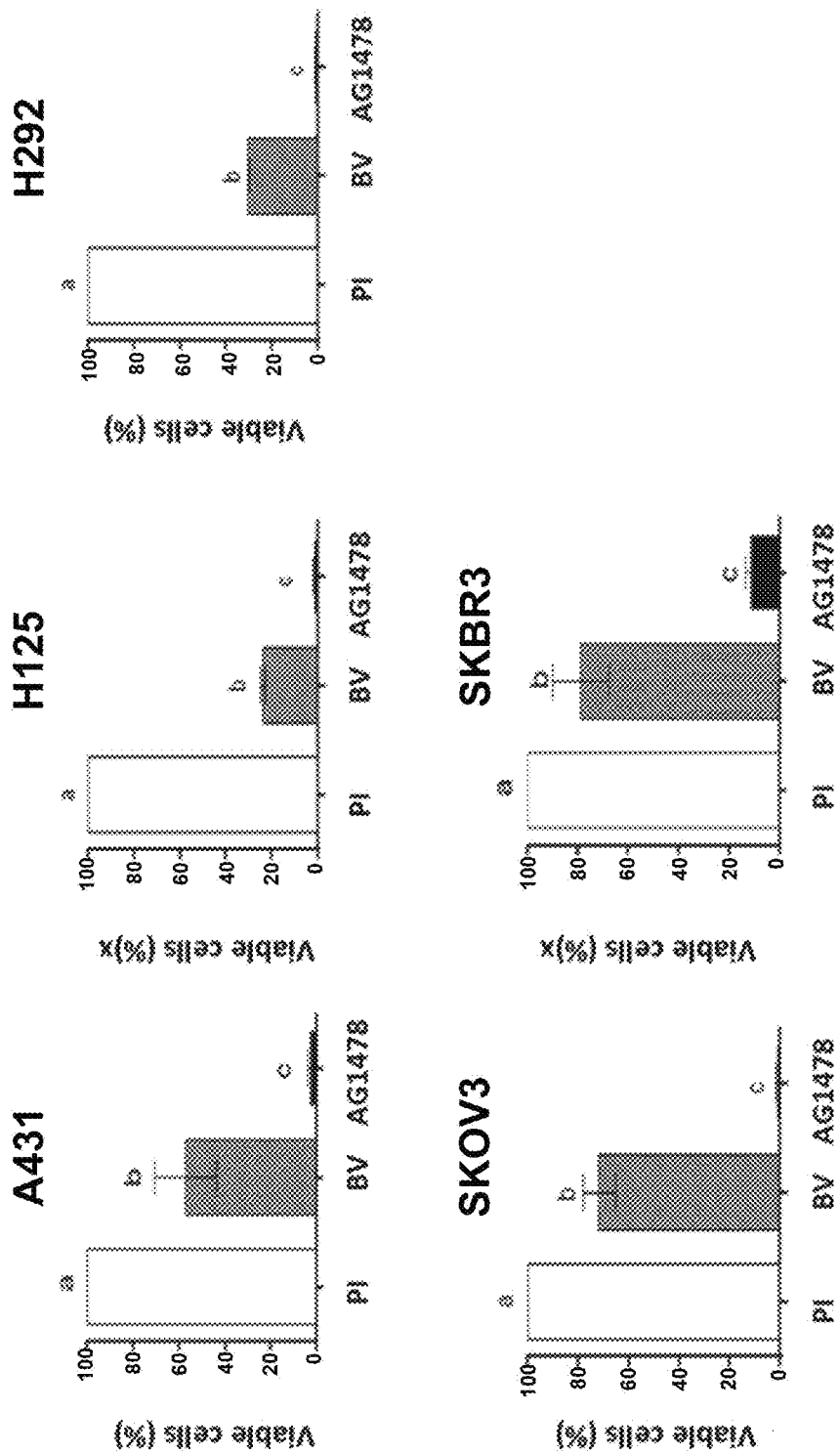
Figure 2C:
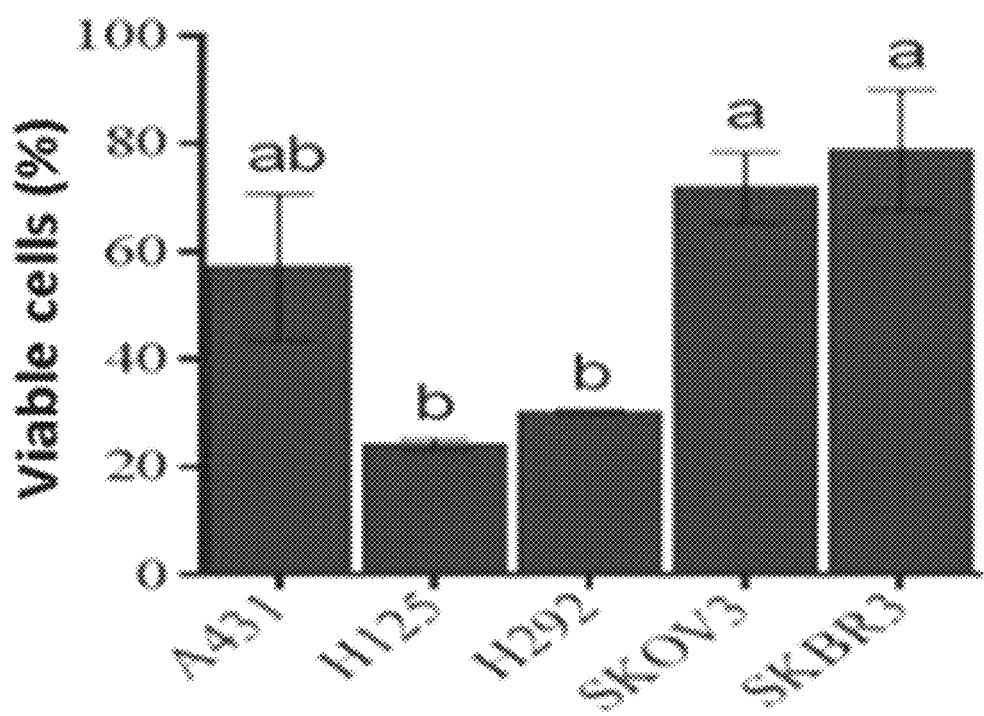

Immune sera from mice immunized with HER1+HER2 BV, diluted 1:20 and heated for 30 min at 56° C. to inactivate the proteins of the complement, were incubated with the tumor lines previously evaluated. The incubation with the sera was carried out for 96 h and the cell viability was determined by the MTT colorimetric method. As control of maximum viability (100%), cells without treatment of each of these lines and incubated under culture conditions were used. The cells treated with a mixture of pre-immune sera (1:20), were considered as negative control of induction of cytotoxicity, associated with the inhibition of HER1 and HER2 while AG1478 tyrosine kinase inhibitor, at a concentration of 10 µM was used as positive control. The immune sera showed impact on the viability of all tumor lines as compared with those treated with the pre-immune sera in which no effect was observed (FIG. 2B). However, the most marked effect on cell viability was obtained on lines that do not show increased expression of any of the HER1 and HER2 receptors: lines H292 and H125, FIG. 2C.

TABLE 1

Levels of expression of HER1 and HER2 in the tumor lines evaluated.

| Cell lines | Expression levels of HER1 | IMF | Expression levels of HER2 | IMF |
|---|---|---|---|---|
| A431 | +++ | 153.27 | + | 1.67 |
| H125 | ++ | 61.77 | + | 1.98 |
| H292 | ++ | 17.92 | + | 2.3 |
| SKOV3 | + | 5.7 | +++ | 31.8 |
| SKBR3 | + | 5.03 | +++ | 50.32 |

Figure 3:
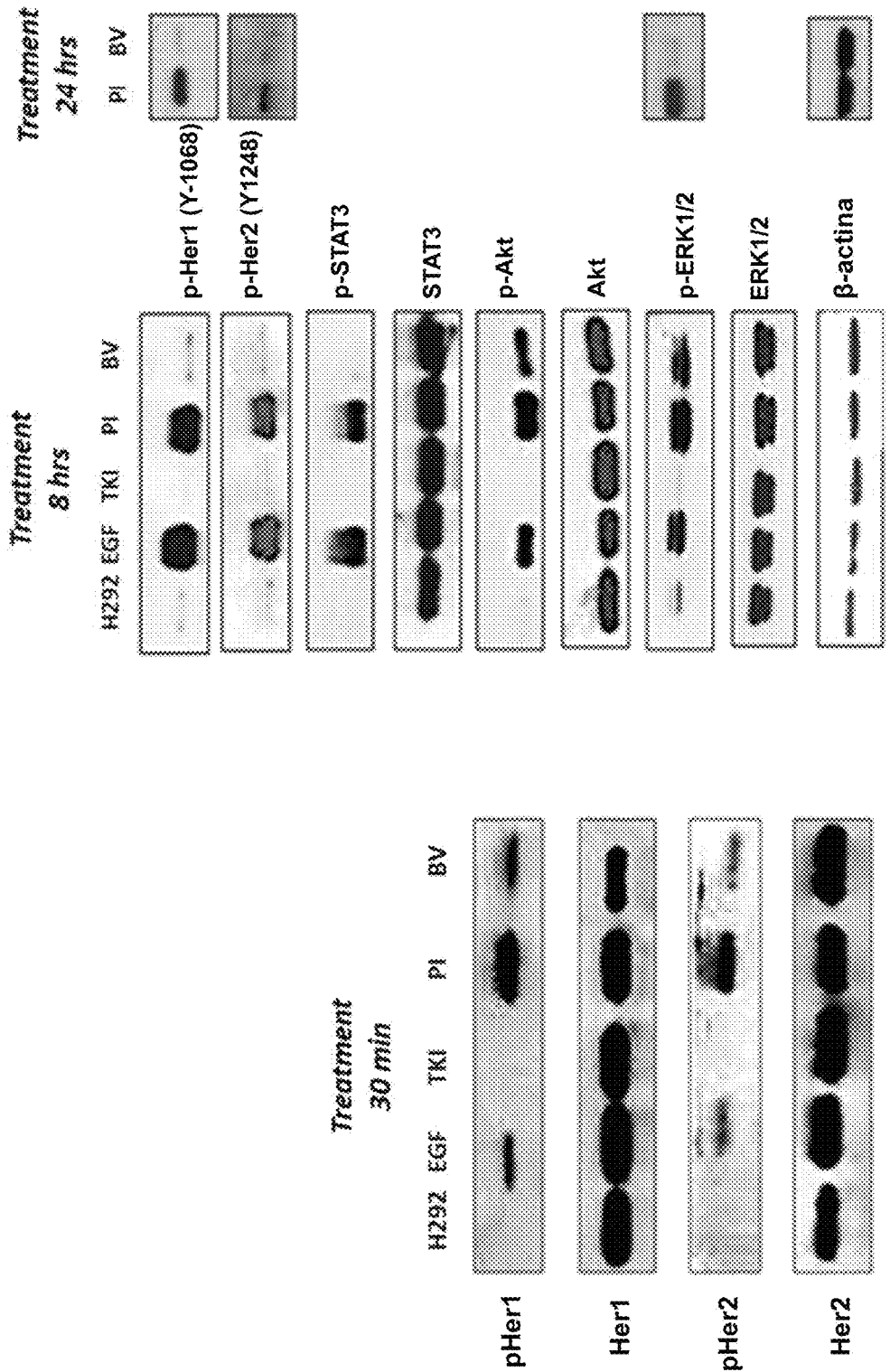
FIG. 3. Inhibition measured by Western Blot in the H292 tumor line of the activation of HER1 and HER2 receptors and signaling cascade proteins, caused by the PAbs of the immune serum induced by the HER1+HER2 BV. PI: Preimmune serum, TKI: tyrosine kinase inhibitor.

Example 3. The PAbs of the Immune Serum Induced by HER1+HER2 BV Inhibit the Activation of HER1 and HER2 Receptors and Proteins of Signaling Cascades Sera from mice immunized with the BV was diluted 1:100 and incubated with cells of the H292 tumor line that co-express the HER1 and HER2 receptors but does not have increased expression of any of these receptors, for 30 min, 8 h and 24 h. The cells were stimulated with 100 ng/mL of EGF for 10 min to induce the activation of HER1 and of the HER2 receptors that were forming heterodimers with HER1. Subsequently, the treated cells were lysed. The effect of the immune sera on the inhibition of the phosphorylation of HER1, HER2, and proteins of the signaling cascades Erk1/Erk2 (MAPK), Akt and STAT3, was determined by means of a Western Blot assay, by the use of antibodies specific for the detection of said phosphorylated proteins. In this assay, the untreated cells were used as negative control of phosphorylation and the cells treated with EGF as positive control. The AG1478 tyrosine kinase inhibitor at 10 µM was used as positive inhibition control and the pre-immune serum was used as a negative control of the specificity of the immune serum. In FIG. 3 it is observed that the sera containing the PAbs generated by the BV inhibited the activation of the HER1 and HER2 receptors, measured in terms of phosphorylation, from as early as 30 min, inhibition that increased markedly with the increase in the treatment time up to 8 h and 24 h. In addition, PAbs markedly inhibited the phosphorylation of Akt and STAT3 proteins, which are key proteins in signal transduction since they are inhibitors of apoptosis and inducers of inflammation, at 8 hours after treatment. Likewise, after 24 h, the total inhibition of the Erk1/Erk2 proteins of the MAPK pathway, inducers of cell proliferation, was observed.

Figure 4:
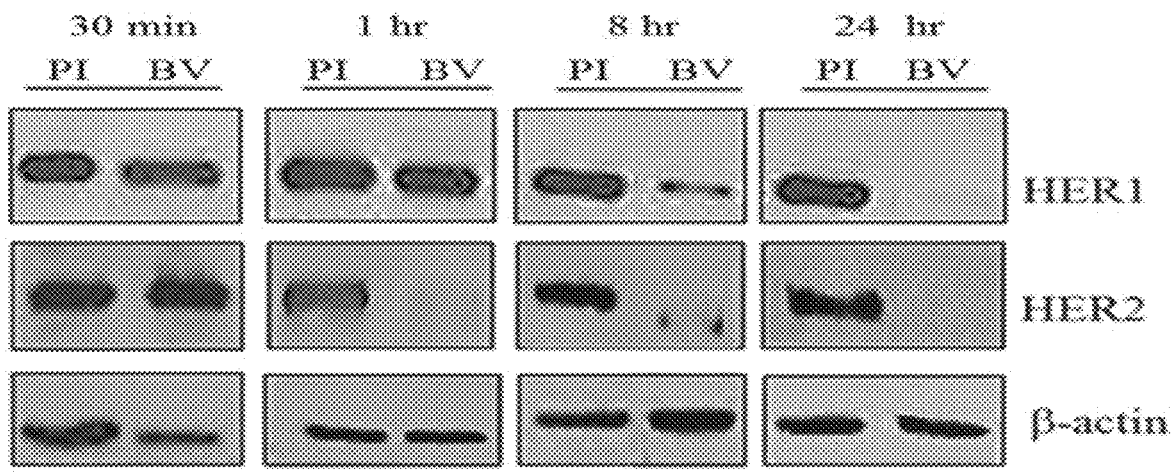
FIG. 4. Effect measured by Western Blot of the PAbs induced by the HER1+HER2 BV on the degradation of the HER1 and HER2 receptors in the H292 tumor line.

Example 4. The PAbs of the Immune Serum Induced by the HER1+HER2 BV Cause Degradation of the HER1 and HER2 Receptors Cells of the H292 tumor line were incubated with mixtures of immune sera (diluted 1:100) induced by HER1+HER2 BV for 30 min, 1, 8 or 24 h. The pre-immune serum was used as negative control in this assay. The expression levels of both receptors at the different times were determined by Western Blot. In FIG. 4 it is observed that the total expression levels of the HER1 and HER2 receptors decreased with the increase of the incubation time with the immune sera, as compared to the cells treated with the pre-immune sera. At 24 hours a total degradation of both receptors was observed.

Figure 5:
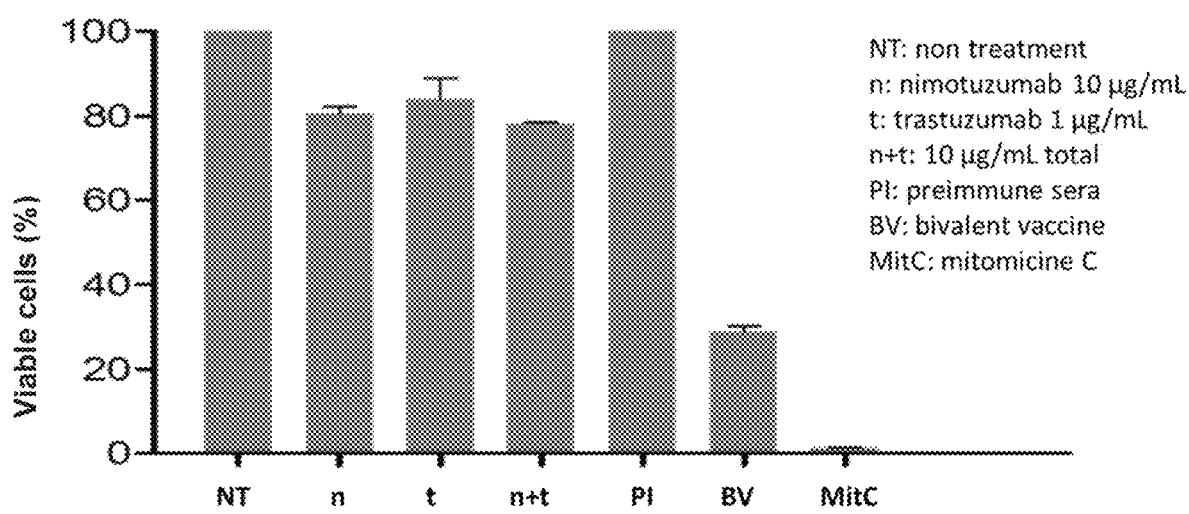
FIG. 5. Comparison of the effect induced by the PAbs generated by the HER1+HER2 BV, the MAbs nimotuzumab and trastuzumab and the combination of both, on the cell viability of the lung carcinoma line H292.

Example 5. Comparison of the Capacity of the PAbs of the Immune Sera with that of the mAbs Nimotuzumab, Trastuzumab and their Combinations of Inhibiting the Viability of Tumor Lines with Low Expression of the HER1 and HER2 Receptors Cells of the H292 tumor line were incubated for 96 h with mixtures of immune sera (diluted 1:100) induced by HER1+HER2 BV. Cell viability was determined by the MTT method. The pre-immune serum was uses as a negative control in this trial. Mitomycin C was used as a positive control of cytotoxicity. The effect of the immune sera was compared with that induced by nimotuzumab mAb, trastuzumab MAb and the mixture of both antibodies. FIG. 5 shows that the immune sera of the HER1+HER2 BV had a greater effect on the viability of the tumor cells than the mAbs and their combination.

Example 6. Comparison of the Capacity of the PAbs of the Immune Sera with that of Nimotuzumab, Cetuximab and Trastuzumab mAbs to Inhibit the Activation of the HER1 and HER2 receptors.

Figure 6:
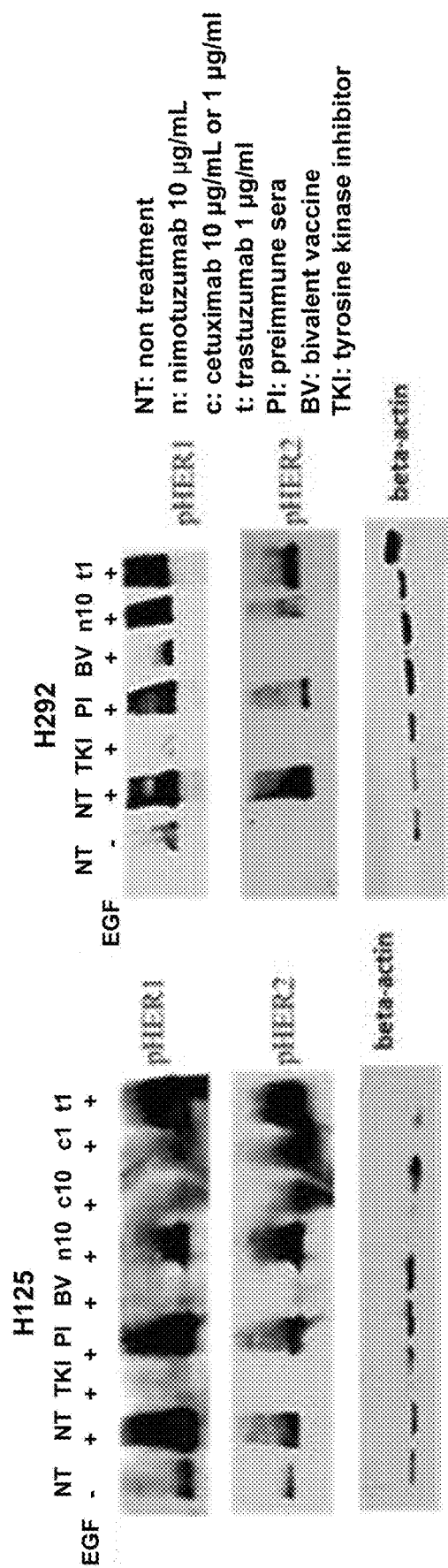
FIG. 6. Comparison measured by Western Blot of the capacity of the PAbs induced by the HER1+HER2 BV and the MAbs nimotuzumab, cetuximab and trastuzumab to inhibit the activation of the HER1 and HER2 receptors in the tumor lines H125 and H292.

Sera from mice immunized with HER1+HER2 BV were diluted 1:100 and incubated for 1 h with cells from the tumor lines H125 and H292 that co-express the HER1 and HER2 receptors but have no increased expression of any of these receptors. This treatment was compared with the treatment with nimotuzumab and cetuximab MAbs, specific for HER1 and with trastuzumab MAb, specific for HER2. The cells were stimulated with 100 ng/mL of EGF for 10 min to induce the activation of HER1 and of the HER2 receptors that were forming heterodimers with HER1. Subsequently, the treated cells were lysed. Inhibition of receptor activation was measured by Western Blot. Cells treated with EGF were used as positive phosphorylation control. The AG1478 tyrosine kinase inhibitor was used as positive inhibition control and the pre-immune serum was used as a negative control of the specificity of the immune serum. FIG. 6 shows that the immune sera of the BV after 1 h of treatment had inhibited more the activation of HER1, measured in terms of phosphorylation, than the MAbs nimotuzumab and cetuximab. Likewise, they inhibited more the activation of HER2 than the MAb trastuzumab.

Figure 7A:
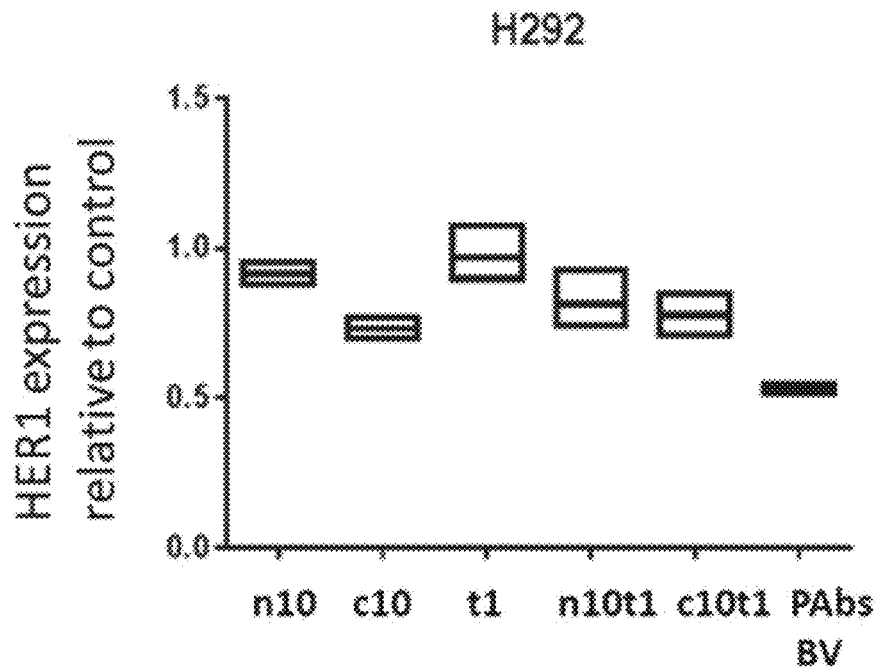
FIGS. 7A-7B. Comparison measured by ELISA of the capacity of the PAbs induced by BV with the MAbs nimotuzumab, cetuximab and trastuzumab to degrade the HER1 and HER2 receptors in the H292 tumor line.
Figure 7B:
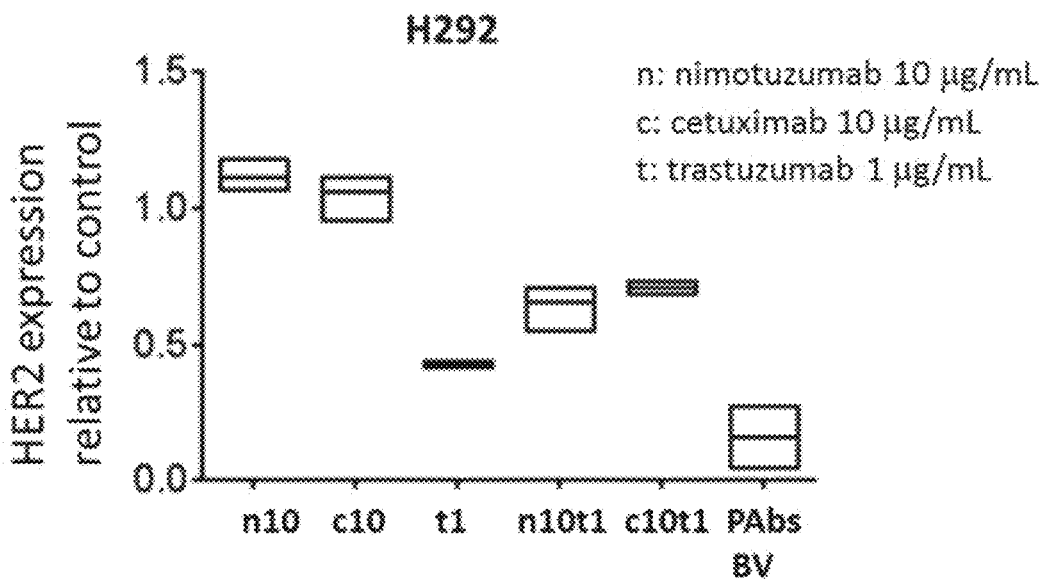

Example 7. Comparison of the Capacity of the PAbs Generated by the HER1+HER2 BV Against that of the AcMs Nimotuzumab, Cetuximab and Trastuzumab to Degrade the HER1 and HER2 Receptors PAbs from the sera of mice immunized with HER1+HER2 BV, at a concentration of 10 μg/mL, were incubated with cells from the H292 tumor line that co-express the HER1 and HER2 receptors but have no increased expression of any of these receptors. This treatment was compared with the treatment with nimotuzumab and cetuximab MAbs, specific for HER1, at the concentration of 10 μg/mL and with cells incubation time of 24 h, and with trastuzumab MAb, specific for HER2, at a concentration of 1 μg/mL and with cells incubation time of 1 h. It was also compared against the combination treatment with nimotuzumab and trastuzumab MAbs, and the combination treatment with the cetuximab and trastuzumab MAbs. In both combinations, the concentration of nimtozumab and cetuximab was 10 ng/mL and that of trastuzumab was 1 μg/mL. The pre-immune serum was used as negative control of specificity. The cells were stimulated with 100 ng/mL of EGF for 10 minutes to induce the activation of HER1 and of the HER2 receptors that were forming heterodimers with HER1. Subsequently, the treated cells were lysed. The degraded receptors were detected by means of the ELISA technique, using a kit of reagents, Quantikine ELISA Human EGFR/ErbB1 Immunoassay to determine the degradation of HER1 and the DuoSet ELISA DEVELOPMENT SYSTEM Human ErbB2/Her2 to determine the degradation of HER2. FIG. 7A shows that the PAbs of the HER1+HER2 BV after 24 h of treatment had degraded more HER1 than nimotuzumab, cetuximab, and tratuzumab MAbs alone and combined. In FIG. 7B it is observed that the PAbs of the HER1+HER2 BV, after 1 h of treatment, degraded more HER2 than nimotuzumab, cetuximab, and tratuzumab MAbs and their combinations.

Figure 8:
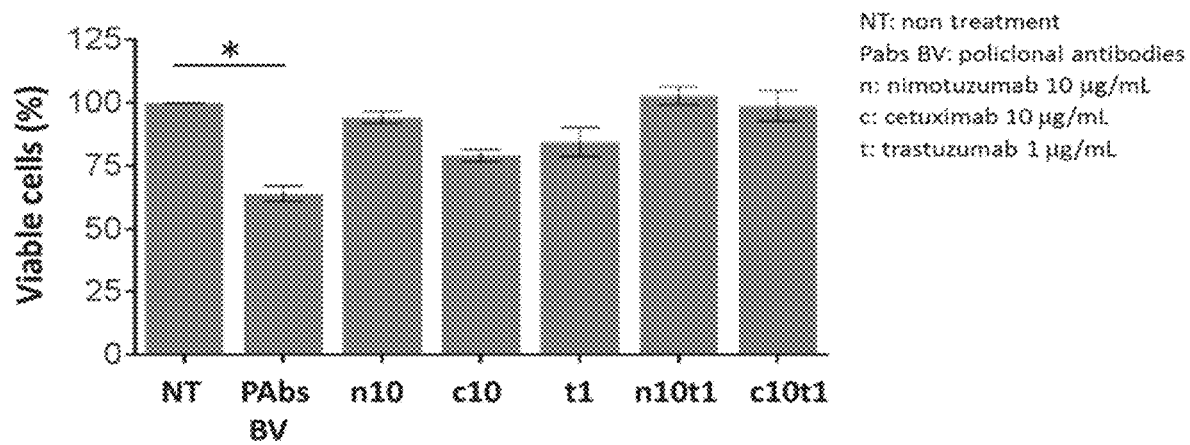
FIG. 8. Comparison of the effect of the PAbs induced by the HER1+HER2 BV on the viability of the KRAS mutated lung carcinoma A549 cell line with the effect of the MAbs nimotuzumab, cetuximab, trastuzumab, and its combinations.

Example 8. Comparison of the Effect Induced by the PAbs of the HER1+HER2 BV on the Viability of the KRAS Mutated Lung Carcinoma A549 Cell Line, Against the Effect of Nimotuzumab, Cetuximab, Trastuzumab mAbs, and their Combinations The PAbs from the serum of mice immunized with the HER1+HER2 BV (10 μg/mL), were incubated for 72 h, with cells from the KRAS mutated lung carcinoma A549 cell line. Cell viability was determined by the MTT method. This treatment was compared against that with nimotuzumab and cetuximab MAbs, at a concentration of 10 μg/mL, and against that with MAb trastuzumab, at a concentration of 1 μg/mL. It was also compared with the combination treatment of nimotuzumab and trastuzumab MAbs, and the combination treatment of cetuximab and trastuzumab MAbs. In both combinations, the concentration of nimotuzumab and cetuximab was 10 μg/mL and that of trastuzumab was 1 μg/mL. As a negative control of the specificity of the PAbs generated by the HER1+HER2 BV, antibodies from the pre-immune sera were used. The % of viable cells resulting from the treatment with the PAbs was normalized against the negative control. FIG. 8 shows that the BV PAbs after 72 h of treatment inhibited the viability of the tumor cells by 40%, whereas cetuximab, nimotuzumab and trastuzumab inhibited only between 20% and 10%. The combinations had no effect on the viability of A549 cells.

Figure 9:
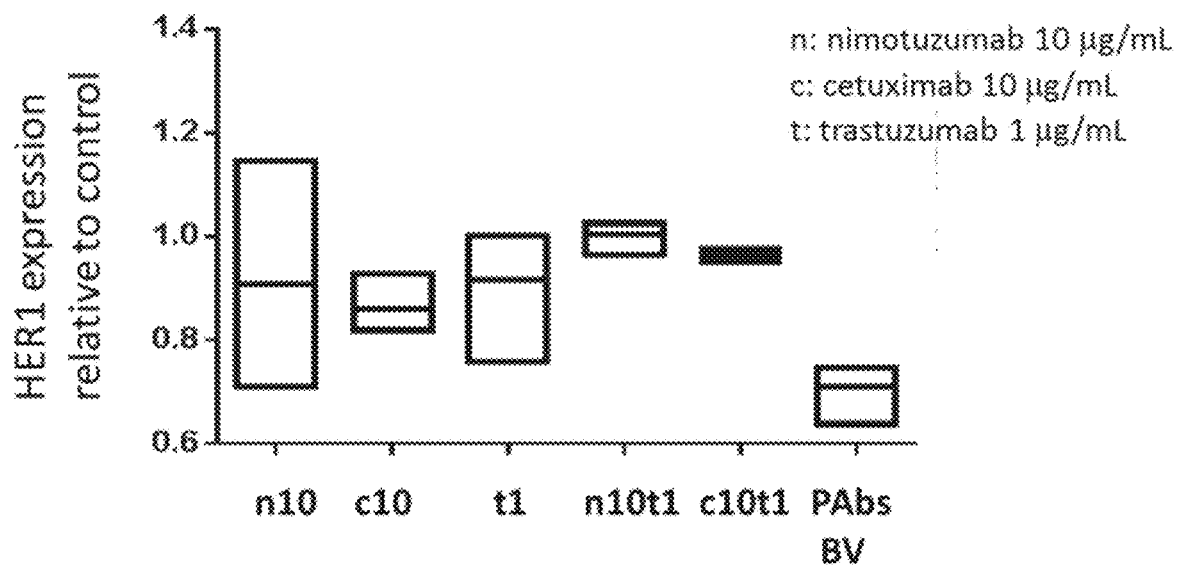
FIG. 9. Comparison of the capacity of the PAbs induced by the HER1+HER2 BV with that of the MAbs nimotuzumab, cetuximab, trastuzumab, and its combinations to degrade the HER1 and HER2 receptors in the KRAS mutated lung carcinoma A549 cell line.

Example 9. Comparison of the Effect Induced by the PAbs of the HER1+HER2 BV on the Degradation of HER1 and HER2, Against the Effect Induced by the Nimotuzumab, Cetuximab, Trastuzumab MAbs, and their Combination PAbs from the sera of mice immunized with HER1+HER2 BV, at a concentration of 10 μg/mL, were incubated for 24 h, with cells from the KRAS mutated lung carcinoma A549 cell line. This treatment was compared with that with nimotuzumab and cetuximab MAbs, at the 10 μg/mL concentration, and against that with trastuzumab MAb, at a concentration of 1 μg/mL. It was also compared with the combination treatment with nimotuzumab and trastuzumab MAbs, and the combination treatment with cetuximab and trastuzumab MAbs. In both combinations, the concentration of nimtozumab and cetuximab was 10 μg/mL and that of trastuzumab was 1 μg/mL. As a negative control of specificity were used the pre-immune sera. The cells were stimulated with 100 ng/mL of EGF for 10 minutes to induce the activation of HER1 and of the HER2 receptors that were forming heterodimers with HER1. Subsequently, the treated cells were lysed. The degraded HER1 receptors were detected by the ELISA technique, Quantikine ELISA Human EGFR/ErbB1 Immunoassay. In FIG. 9 it is observed that the PAbs induced by HER1+HER2 BV after 24 h of treatment had degraded more HER1 than nimotuzumab and cetuximab MAbs, alone or combined with trastuzumab MAb.

The invention claimed is:

1. A method for treating a patient with carcinoma of the lung comprising:
   a) determining whether the patient diagnosed with the carcinoma of the lung is likely to respond or not to treatment with a bivalent vaccine (By) composition having as active ingredient extracellular domains of HER1 and HER 2 receptors and as adjuvant proteoliposomes derived from the outer membrane proteins of *Neisseria meningitidis* and GM3 ganglioside, which comprises a step of determination in a sample taken from said patient the presence of:
   activating mutations in RAS and
   b) administration of said BV composition to said patient determined to have activating mutations in RAS.

2. The method according to claim 1 wherein the BV is administered subcutaneously, intradermally or intramuscularly with weekly during the first five doses followed by monthly doses of maintenance by at least six months by subcutaneous, intradermal or intramuscular route.

3. The method according to claim 1 wherein the patient shows a complete or partial response after the administration of 9 doses of the BV.

* * * * *